US012575723B2

(12) United States Patent
Loewen et al.

(10) Patent No.: US 12,575,723 B2
(45) Date of Patent: Mar. 17, 2026

(54) LIGHTED BOUGIE

(71) Applicants: John Loewen, Santa Rosa, CA (US);
Frank LoVecchio, Phoenix, AZ (US);
Keith A. Cardinal, Phoenix, AZ (US)

(72) Inventors: John Loewen, Santa Rosa, CA (US);
Frank LoVecchio, Phoenix, AZ (US);
Keith A. Cardinal, Phoenix, AZ (US)

( * ) Notice: Subject to any disclaimer, the term of this
patent is extended or adjusted under 35
U.S.C. 154(b) by 1990 days.

(21) Appl. No.: 16/465,348

(22) PCT Filed: Nov. 30, 2017

(86) PCT No.: PCT/US2017/063929
§ 371 (c)(1),
(2) Date: May 30, 2019

(87) PCT Pub. No.: WO2018/102541
PCT Pub. Date: Jun. 7, 2018

(65) Prior Publication Data
US 2019/0388635 A1      Dec. 26, 2019

Related U.S. Application Data

(60) Provisional application No. 62/428,423, filed on Nov.
30, 2016.

(51) Int. Cl.
*A61B 1/06*          (2006.01)
*A61B 1/05*          (2006.01)
(Continued)

(52) U.S. Cl.
CPC .............. *A61B 1/06* (2013.01); *A61B 1/0615*
(2013.01); *A61B 1/0669* (2013.01); *A61B 1/07*
(2013.01);
(Continued)

(58) Field of Classification Search
CPC ......... A61B 1/06; A61B 1/0676; A61B 1/105;
A61B 2090/304; A61B 5/0836; A61B
5/14539
See application file for complete search history.

(56) References Cited

U.S. PATENT DOCUMENTS 5,277,173 A * 1/1994 Cantele .................. A61B 1/267
600/199
5,819,727 A * 10/1998 Linder .............. A61M 16/0488
128/207.14
(Continued)

OTHER PUBLICATIONS

Jeanette Scott, Orlando R. Hung, Intubating Inducers, Stylets, and
Lighted Stylets (Lightwands), clinicalgate.com, Feb. 27, 2015,
Chapter 21, https://clinicalgate.com/intubating-introducers-stylets-
and-lighted-stylets-lightwands/.

*Primary Examiner* — Eduardo C Robert
*Assistant Examiner* — Holly Joanna Lane
(74) *Attorney, Agent, or Firm* — Messner Reeves LLP;
Scott J. Hawranek

(57)          ABSTRACT

A bougie having the dimensions of a standard bougie used
widely by first responders is further configured to emit tight
with an intensity that transilmminates a patient's neck; thus
the position of the bougie is visible to the first responder
when placed in the patient's airway. The bougie includes a
light source, which may be a luminescent chemical combi-
nation contained in a chamber of the bougie. The lumines-
cent chemical may have a high intensity and a short dura-
tion. The light source may be a light-emitting diode powered
by an onboard battery and emitting light into a fiber-optic
cable that emits light from the distal end and/or from
interruptions in a reflecting coating that allows transverse
exit of some of the light. The light source may be a
chemilmninescent material or compound. All components of
(Continued)

the bougie are sized to pass through an endotracheal tube without removing any of the components.

20 Claims, 3 Drawing Sheets

(51) Int. Cl.

| | | |
|---|---|---|
| *A61B 1/07* | (2006.01) | |
| *A61B 90/30* | (2016.01) | |
| *A61M 16/04* | (2006.01) | |
| A61B 5/083 | (2006.01) | |
| A61B 5/145 | (2006.01) | |

(52) U.S. Cl.
CPC ........... *A61M 16/0488* (2013.01); *A61B 1/05* (2013.01); *A61B 5/0836* (2013.01); *A61B 5/14503* (2013.01); *A61B 5/14539* (2013.01); *A61B 2090/304* (2016.02); *A61M 2205/582* (2013.01); *A61M 2205/587* (2013.01)

(56) References Cited

U.S. PATENT DOCUMENTS

| | | | | | |
|---|---|---|---|---|---|
| 7,052,456 | B2 | | 5/2006 | Simon | |
| 7,243,653 | B2 * | | 7/2007 | Nelson | A61M 16/04 |
| | | | | | 128/207.14 |
| 7,650,886 | B1 * | | 1/2010 | Keller | A61M 16/0493 |
| | | | | | 128/207.14 |
| 8,746,239 | B2 * | | 6/2014 | Yoshida | A61M 16/04 |
| | | | | | 128/207.14 |
| 2007/0175482 | A1 | | 8/2007 | Kimmel et al. | |
| 2008/0017195 | A1 * | | 1/2008 | Yoshida | A61M 16/0418 |
| | | | | | 128/200.26 |
| 2010/0094090 | A1 * | | 4/2010 | Mejia | A61B 1/0014 |
| | | | | | 600/156 |
| 2010/0108060 | A1 * | | 5/2010 | Pecherer | A61M 16/0488 |
| | | | | | 128/200.26 |
| 2011/0028790 | A1 * | | 2/2011 | Farr | A61B 1/0676 |
| | | | | | 600/187 |
| 2011/0120459 | A1 * | | 5/2011 | Ramos | A61M 25/0102 |
| | | | | | 29/454 |
| 2012/0016197 | A1 | | 1/2012 | Turnbull | |
| 2012/0298102 | A1 * | | 11/2012 | Levitan | A61M 16/0472 |
| | | | | | 128/200.26 |
| 2013/0041227 | A1 | | 2/2013 | Chan et al. | |
| 2013/0081614 | A1 * | | 4/2013 | O'Mara | A61M 16/0488 |
| | | | | | 128/200.26 |
| 2014/0073858 | A1 * | | 3/2014 | Sherwinter | A61B 1/06 |
| | | | | | 600/249 |
| 2014/0378792 | A1 * | | 12/2014 | Krimsky | A61L 2/10 |
| | | | | | 128/200.26 |
| 2015/0034078 | A1 * | | 2/2015 | Sovndal | A61M 16/0488 |
| | | | | | 128/200.26 |
| 2015/0238088 | A1 * | | 8/2015 | Hufnagel | A61B 5/4836 |
| | | | | | 600/476 |
| 2017/0196486 | A1 * | | 7/2017 | Anderson | A61B 5/0215 |

* cited by examiner

LIGHTED BOUGIE

CROSS-REFERENCE TO RELATED APPLICATIONS

This application represents the national stage entry of PCT International Application No. PCT/US2017/063929, filed on Nov. 30, 2017, which claims priority to U.S. Prov. Pat. App. Ser. No. 62/428,423, filed Nov. 30, 2016, each of which is incorporated fully herein by reference.

BACKGROUND OF THE INVENTION

The present invention relates to endotracheal introducers, and specifically to a disposable, lighted introducer having the recognizable characteristics of existing introducers known as "bougies" used in hospitals and especially by first responders. The need for first responders and Emergency Department (ED) personnel, as well as physicians and nurses in hospital settings, to rapidly obtain an airway in patients where respiratory function has been compromised has long been established. There are situations where traditional methods of intubation utilizing a laryngoscope and inserting an endo-tracheal tube are ineffective or impractical due to the inability to visualize the vocal cords or pass the tube properly into the trachea. This difficulty can be caused by trauma and/or body habitus, among many other causes.

When the vocal cords cannot be visualized using traditional methods, health care practitioners and/or first responders have relied on several different tools to help facilitate the successful establishment of an airway. The use of a stylet, lighted or otherwise as an intubation assist device, a laryngeal mask airway (LMA), as well as a rubber or soft bougie with or without a curved distal end have been seen in various forms. The use of various methods of achieving luminescence to the introducing device typically include means of a single point light source, typically, but not always located at the distal end to achieve translumination of the outer surface of the neck through the larynx to assure proper placement. These methods aim to assure that the introducer is placed properly in the trachea as opposed to being introduced to the esophagus. Existing solutions for facilitating, better visualization and assurance of a properly placed introducer have proven to be too costly, difficult to use in the field as well as in a medical facility, or too complicated in design to be practical for use by fully equipped ED personnel, let alone first responders under extremely adverse conditions.

Therefore, what is needed is an introducer for use in establishing and verifying a proper path for intubation by means of trans-illumination of the exterior surface of the neck in first responder, emergency department, hospital, and other medical situations where traditional intubation methods are currently used but are impossible, impractical, or inefficient.

SUMMARY OF THE DISCLOSURE

The foregoing needs are met by the methods, apparatus, and/or systems described herein for establishing and verifying a proper path for intubation using a disposable lighted bougie having a form factor that is fundamentally indistinguishable from that of the traditional unlighted bougie currently widely used by emergency department (ED) personnel and first responders, as well as by physicians and nurses in hospitals and other medical facilities. In particular, the present design of a luminescent disposable endo-tracheal bougie that is as close in shape and design as current non-illuminated bougies can be readily recognized by ED personnel, first responders, nurses, anesthesiologists, and other healthcare providers, by both sight and touch, allowing for quick deployment. The present lighted bougie requires no specialized ancillary equipment or training to use. Due to the ability to trans-illuminate not only at the distal end, but along a substantial portion or even the entire length of the bougie, the location in the trachea of the bougie from the coudete to the distal end can be seen through the skin throughout the introducer process. Additionally, once the pathway is established, a traditional endotracheal tube can be easily introduced directly over the bougie, and the bougie removed, without additional complicated procedures, such as the removal of a power source used to provide the trans-illuminating light.

The present lighted bougie maintains the capabilities, due to design, of traditional bougies by being so shaped and constructed as to provide to the technician well-known audible and/or tactile feedback indicative of correct placement in the trachea—in particular, the recognized bougie profile having a fixed bend near the distal end generates a "click," which the technician can hear and/or feel, when the bougie engages a tracheal ring. Further, the present lighted bougie is shaped so the technician can easily deploy a traditional tube over the introducer once the airway is established. The present lighted bougie provides, relative to known existing comparable devices, a greatly improved method of trans-luminescence, more ergonomic deployment, disposability and portability. These improvements are achieved, for example, by providing the following features, alone or in combination, in various embodiments.

The bougie may itself be the source of illumination, being in one embodiment a rod being constructed of a thermoplastic resin with fiber optic properties, eliminating the need for a fiber optic bundle to be incorporated into the design. An alternate embodiment may include an electro-luminescent coating on the inner layer of a multiple-layer extruded rod, the coating being excited upon the application of current to embedded conductors in the coating and producing illumination. Another alternate embodiment may utilize a high intensity chemical light, as in light stick technology, which may be fully enclosed and may not have the capability of generating heat.

The light source may be simplified, such as in one or more high intensity LEDs located at the proximal end in an integral housing that also holds the power source. The power source may also be simplified. The diameter of the power source, LED or LED array, and housing may be no larger than an inner diameter of an endotracheal tube, such that the bougie passes through the endotracheal tube without removal of the power source, LEDs, housing, or any other component of the bougie. The bougie may further have about the same weight, measured for example by inch of length, as a traditional bougie. Alternative embodiments may also have no dimensional aberrations from traditionally recognized bougies. This allows this invention to have approximately or relatively the same ergonomic "feel" and center of mass as the traditional unlighted gum bougie, minimizing any training or re-fitting of rigs to use the device, and avoiding any impediment to adoption by the First Responder community.

The area of trans-illumination may be controlled by interrupting an over-molded surface of the bougie, exposing a light pipe at the point desired, thus controlling one or more points at which light emanates from the bougie. A sensor may receive and amplify the laryngeal clicks as the tube passes the laryngeal rings indicating proper placement. This could be augmented by haptic feedback, felt in the bougie proximal end by the vibration of a haptic response sensor. Light sensors and/or imaging devices fitting within the diameter of the bougie may actively or passively allow for the transmission of a video image from the distal end of the bougie by utilizing one fiber optic core to receive the image. The fiber optic core may have over extruded the fiber optic polymer as described above which would provide the aforementioned illumination. This layer may be over-extruded with a cladding to provide desired stiffness and coefficient of friction to the structure.

Thus, the described lighted bougie is a unique improvement over prior attempts at lighted stylets or bougies in that it maintains the footprint of traditional bougies, utilizes a self-contained power source and method of illumination. In the preferred embodiment it is comprised of a solid fiber optic polymer which improves upon prior art currently requiring bundled fiber optic cables. In the proposed invention, the bougie itself is constructed of a fiber optic rod which transmits light to the exposes distal end of the bougie, thus eliminating the need for additional fiber optic bundles. The light source is reduced to a high intensity LED in a housing located at the proximal end and having the same or approximately the same diameter as the bougie providing the power source as well. Therefore no removal of the light source for introduction of the ET tube is required once an airway path has been established. Other stated embodiments would provide illumination in the same self-contained fashion. All would be designed to be self-activating upon opening the packaging or removing a pull tab, requiring no additional work on the part of the technician utilizing the device.

In one aspect, the present disclosure therefore provides a bougie for locating an airway of a patient. The bougie includes: a proximal end and a distal end, the bougie from the proximal end to the distal end having a standard diameter that enables a user of the bougie to pass the bougie through an endotracheal tube that is placed in the patient's airway using the bougie; a fixed bend near the distal end; and, a light source having a sufficient light intensity and positioned to provide transillumination of an outer surface of the patient's neck when the bougie is positioned in the patient's airway. The light source may be a chemical light, and the bougie may further include a light-transmissive casing containing the chemical light and disposed relative to the distal end of the bougie such that light from the chemical light is visible on the outer surface of the patient's neck when the bougie is inserted into the patient's airway. The chemical light may be configured to illuminate when the bougie is deployed, and may have a duration of about five minutes. The chemical light may include one or more luminescent chemicals that, taken alone or together, are non-toxic to the patient; the casing may be a transparent or translucent tube defining a chamber that contains the one or more luminescent chemicals.

The bougie may further include a proximal portion extending from the proximal end of the bougie to the casing. The proximal portion may be a polymer that attaches to the casing, or the proximal portion may be integral with the casing. The bougie may further include a distal portion extending from the distal end of the bougie to the casing. The proximal portion, the easing, and the distal portion may all have the same uniform diameter.

The bougie may further include a device for detecting conditions at the distal end of the bougie; the device may be a carbon dioxide sensor, a pH sensor, or an imaging device.

The bougie may further include a haptic feedback device disposed near the distal end of the bougie, the haptic feedback device detecting when the distal end passes over a laryngeal ring and producing a haptic feedback response.

The bougie may further include: a housing disposed at the proximal end of the bougie and containing the light source; a power source disposed at least partially within the housing, sized to pass through the endotracheal tube, and electrically connected and providing power to the light source; and, a fiber-optic cable extending from the housing to the distal end of the bougie and having a light-emitting portion approximate the distal end of the bougie, the fiber-optic cable and the light source oriented so that light emitted from the light source enters the fiber-optic cable, is transmitted to the light-emitting portion, and exits the fiber-optic cable to transilluminate the outer surface of the patient's neck. The fiber-optic cable may be an end-emitting elastomeric solid rod that includes the fixed bend; the bougie may further include a light-transmissive outer layer disposed over at least part of the fiber-optic cable and having the standard diameter. The housing may be a cylindrical case having the standard diameter and abutting the outer layer. The outer layer may be further disposed over the housing. The fiber-optic cable may extend beyond the outer layer to form the distal end of the bougie, and may be rounded and polished to emit light from the distal end of the bougie. The bougie may further include a coating, disposed on the fiber-optic cable and restricting transverse transmission of light out of the fiber-optic cable. The bougie may further include one or more longitudinal interruptions formed through the coating, the one or more longitudinal interruptions allowing light to exit transversely from the fiber-optic cable.

In another aspect, the present disclosure provides a method for intubating a patient. The method includes the steps of: activating a lighted bougie; positioning the distal end of the lighted bougie in the patient's mouth approximate the patient's trachea; using the light emitted from the light source and visible through the patient's neck, inserting the lighted bougie into the patient's trachea; and, without removing any components of the lighted bougie, positioning the endotracheal tube over the lighted bougie and into the patient's trachea and removing the lighted bougie from the patient's trachea and from the endotracheal tube. The lighted bougie activated during the method includes: a proximal end and a distal end, the bougie from the proximal end to the distal end having a standard diameter that enables a user of the bougie to pass the bougie through an endotracheal tube that is placed in the patient's airway using the bougie; a fixed bend near the distal end; and, a light source having a sufficient light intensity and positioned to provide transillumination of an outer surface of the patient's neck when the bougie is positioned in the patient's airway.

These and other aspects of the invention will become apparent from the following description. In the description, reference is made to the accompanying drawings which form a part hereof, and in which there is shown embodiments of the invention. Such embodiments do not necessarily represent the full scope of the invention and reference is made therefore, to the claims herein for interpreting the scope of the invention.

BRIEF DESCRIPTION OF THE DRAWINGS

The present disclosure will hereafter be described with reference to the accompanying drawings, wherein like reference numerals denote like elements.

DETAILED DESCRIPTION

Before the present invention is described in further detail, it is to be understood that the invention is not limited to the particular aspects described. It is also to be understood that the terminology used herein is for the purpose of describing particular aspects only, and is not intended to be limiting. The scope of the present invention will be limited only by the claims. As used herein, the singular forms "a", "an", and "the" include plural aspects unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising", "including", or "having" should be interpreted as referring to elements, components, or steps in a non-exclusive manner, so the referenced elements, components, or steps may be combined with other elements, components, or steps that are not expressly referenced. Aspects referenced as "comprising", "including", or "having" certain elements are also contemplated as "consisting essentially of" and "consisting of" those elements, unless the context clearly dictates otherwise. It should be appreciated that aspects of the disclosure that are described with respect to a system are applicable to the methods, and vice versa, unless the context explicitly dictates otherwise.

Numeric ranges disclosed herein are inclusive of their endpoints. For example, a numeric range of between 1 and 10 includes the values 1 and 10. When a series of numeric ranges are disclosed for a given value, the present disclosure expressly contemplates ranges including all combinations of the upper and lower bounds of those ranges. For example, a numeric range of between 1 and 10 or between 2 and 9 is intended to include the numeric ranges of between 1 and 9 and between 2 and 10.

Figure 1:
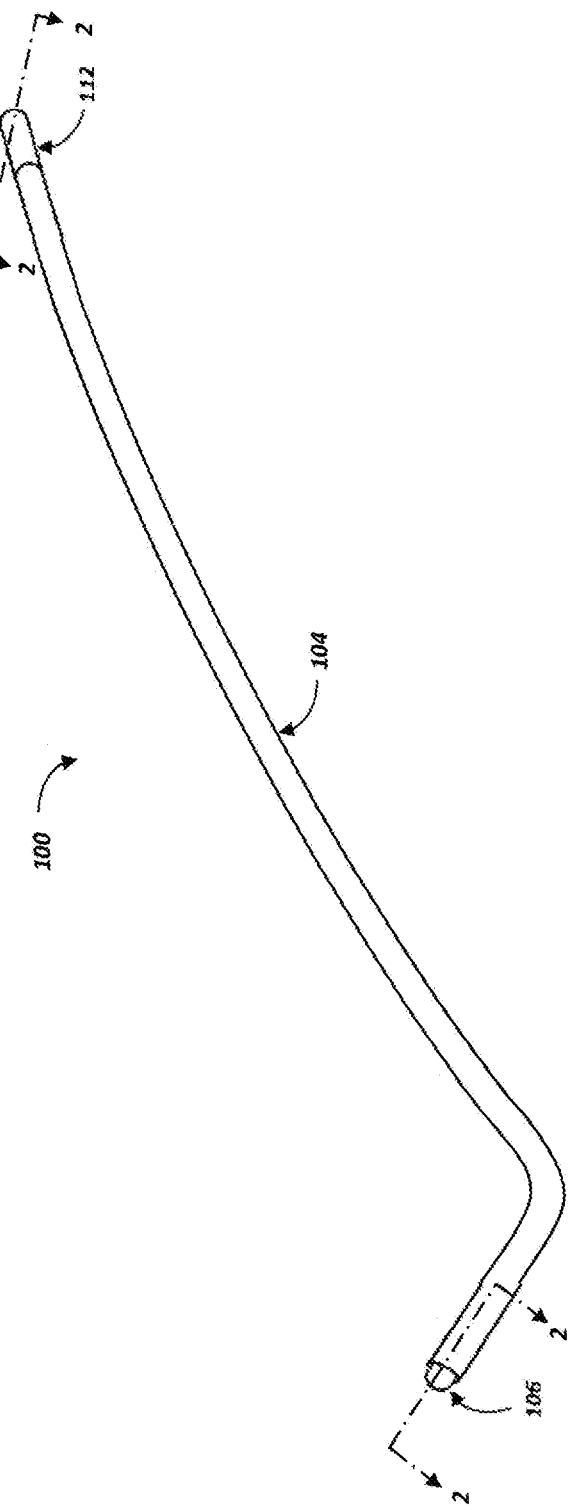
FIG. 1 is a perspective view of a lighted bougie according to one embodiment of the disclosure.
Figure 2:
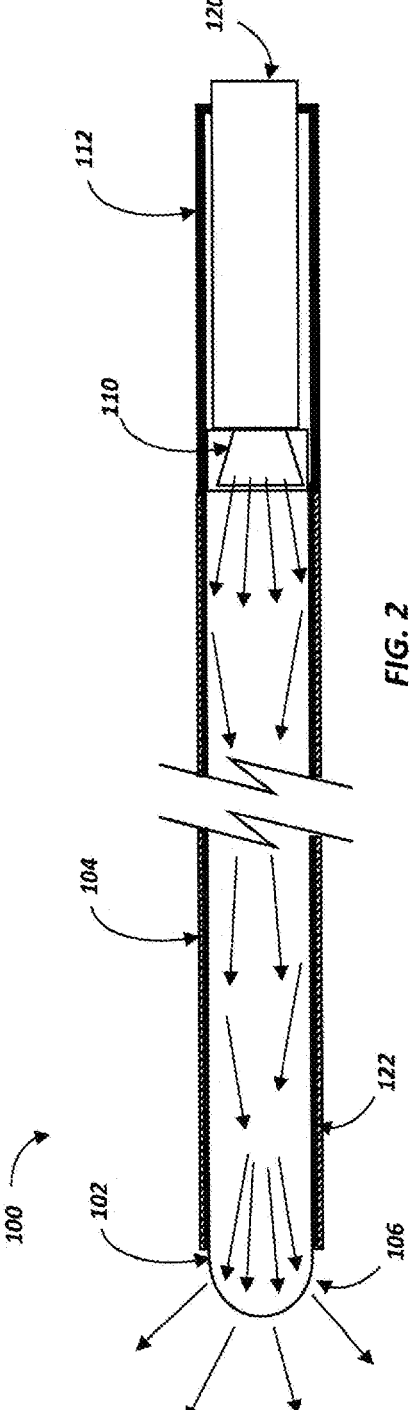
FIG. 2 is a cross-sectional schematic view of the lighted bougie of FIG. 1 taken along lines 2-2 and showing the path of light within the fiber-optic cable.
Figure 3:
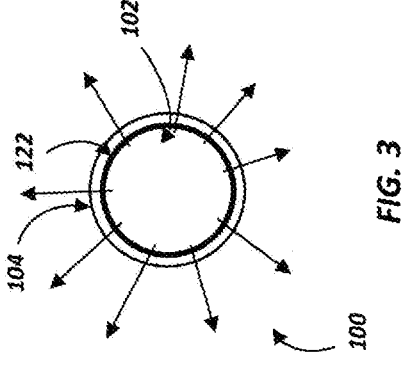
FIG. 3 is a front (i.e., distal-end) view of the lighted bougie of FIG. 2.

FIGS. 1-3 show perspective and cross-sectional views of a lighted bougie 100 according to one embodiment of the disclosure. The lighted bougie 100 may be a malleable elastomeric solid rod having a fixed bend near the distal end, according to existing widely-adopted bougies. The rod may be constructed of an end-emitting fiber-optic cable 102 (see FIG. 2) that may be solid, moldable, extrudable, and capable of transmitting light both axially along the length of the cable 102 and transversely across or radially from the axis or outer surface of the cable 102 toward an outer layer 104 disposed over the cable 102. In some embodiments, the outer layer 104 may be a coating or jacket; in other embodiments, the outer layer 104 may be cladding.

The cable 102 may additionally or alternatively be coated or over-molded with a coating 122 of lubricating resin, such as a thermoplastic elastomer (TPE) or a perfluoroalkoxy polymer resin (PFA), which may restrict the transverse transmission of light out of the side of the cable 102 and/or redirect incident light along the longitudinal axis of the cable 102. The coating 122 or over-molding may be disposed between the cable 102 and the outer layer 104. The over-molded area may be interrupted either mechanically or in the molding process so as to allow light to pass through the wall of the cable 102 at a point or points longitudinally near the distal end 106 of the cable 102. The distal end 106 may extend beyond the outer layer 104, and may be highly polished and rounded to transmit the maximum intensity of light. This light would be visible on the outer surface of the patient's neck when the bougie 100 is correctly placed in the trachea. The longitudinal interruptions may also form a glide path indicating relative placement in the trachea—for instance, that the bougie 100 was centered and not mistakenly inserted into one lung.

A light source 110 may in some embodiments be a single high-intensity LED disposed within a housing 112. The light source 110 may be disposed adjacent to a proximal end of the cable 102 and may be coupled to the cable 102 so as to emit light into the cable 102. The housing 112 may be a cylindrical case of a diameter equal to or slightly larger than the corresponding bougie size (defined by the outer diameter of the outer layer 104) for which the housing 112 is designed, but smaller than the inner diameter of the corresponding endo-tracheal tube for which the bougie 100 is designed, so that the endo-tracheal tube can be inserted over the bougie 100. The housing 112 may also partially or fully contain or support a power source 120 electrically connected to the light source 110. The power source 120 may be a pin battery or other micro or printed battery technology containing sufficient energy to cause the light source 110 to illuminate for at least a desired duration. The power source 120 further may have a diameter that at no point within the power source 120 is larger than the outer diameter of the outer layer 104.

The housing 112 may be an integral part of the bougie 100, such as by disposing all or a portion of the housing 112 inside the outer layer 104 and affixing the housing 112 to the outer layer 104 or to the cable 102 such that light is transmitted down (i.e., toward the distal end 106 of) the cable 102 during introduction of the bougie 100 into a patient's airway. This design allows for easy deployment of the bougie 100, enhanced visualization of correct placement and no need to remove any components of the bougie 100 for introduction of the endo-tracheal tube and removal of the bougie 100 once the path to the trachea has been established. The methods of using the bougie 100 may be substantially identical to those for non-illuminated bougies, as the dimensions, weight, and flexibility of the bougie 100 is approximately or relatively the same as existing designs. The light source 110 may be activated to illuminate the bougie 100 for deployment by opening a sterile package containing the bougie 100, or by removing a tab separating the light source 110 from the power source 120 without additional steps required on the part of the technician. For example, the bougie 100 may be packaged in a sterile, sealed pouch with a tab affixed to an inner surface of the pouch and disposed between the light source 110 and the power source 120; when the pouch is pulled open, the tab is pulled out and the power source 120 makes electrical contact with and activates the light source 110. The bougie 100 may be introduced in the same fashion as current bougies with the added benefit of being able to positively verify that the bougie 100 has been correctly placed prior to attempting to place an endotracheal tube over the bougie 100 to complete the intubation.

Alternative embodiments of the bougie 100 may use one or more electro-luminescent coatings, such as Lumilor® or an electroluminescent polymer, in or on an inner layer or outer layer 104 of the bougie 100. The coating may illuminate upon application of energy from the power source 120 to embedded conductors in the resin or coating 122. Still another embodiment for illumination, described further below, would utilize a chemical light disposed within a casing of the bougie.

Figure 4:
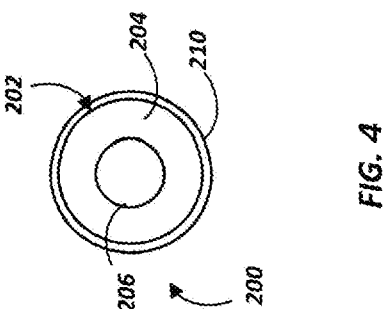
FIG. 4 is a front cross-sectional view of another embodiment of a lighted bougie in accordance with the present disclosure.

FIG. 4 illustrates a transverse cross section of an alternative exemplary embodiment of a lighted bougie 200. Instead of a "solid core" fiber-optic cable as in the embodiment described above, the bougie 200 may comprise a fiber-optic cable 202 having two solid, concentric light-transmitting layers: an outer layer 204 may be used to transmit light from the proximal end to the distal end of the cable 202 as described above; and, an inner layer 206 may receive light reflected back into the distal end of the cable 202 and transmit the reflected light to an image sensor (not shown) at the proximal end of the bougie 200. This sensor may use video capture and transmission technology, such as currently used in casting devices, to detect an image in the reflected light, which may assist in locating the bougie 200 by direct illumination of the trachea during introduction. It would also be intended to be compatible with virtual and/or augmented reality devices providing direct and trans-illumination simultaneously. Additionally or alternatively, an imaging device such as a camera may be positioned at the distal end of the lighted bougie 200. The imaging device may have a width no larger than the diameter of the outer layer 204, so as not to increase the overall diameter of the bougie 200. The imaging device may be in signal communication with the inner layer 206, or may transmit recorded data (i.e., images of the airway) to a viewing device, such as a mobile computer screen, via a wireless connection. An outer cladding 210 may be disposed over the outer layer 204.

Figure 5:
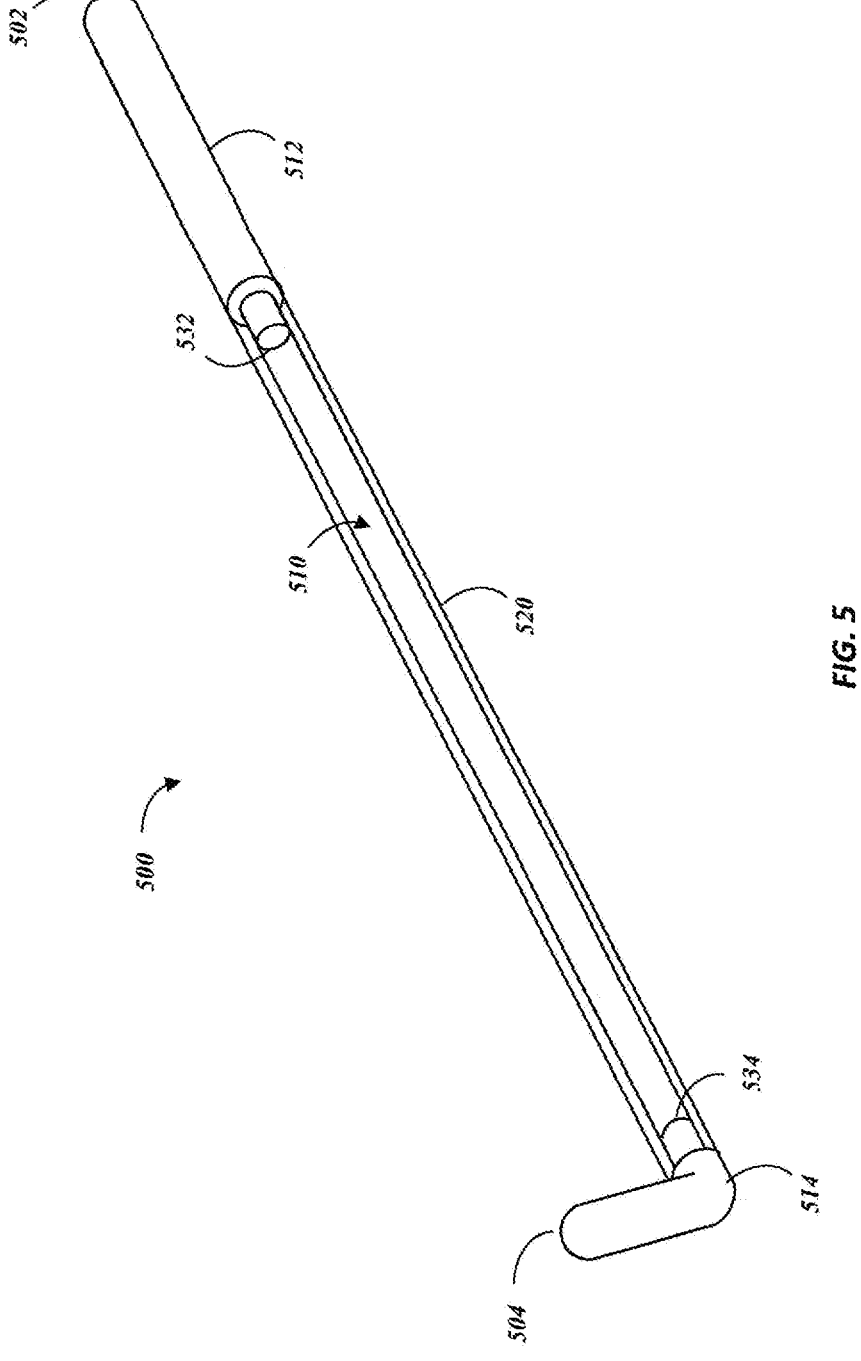
FIG. 5 is a perspective view of a lighted bougie according to yet another embodiment of the disclosure.

FIG. 5 illustrates another embodiment of a lighted bougie 500 which, for illumination, uses a high intensity, short duration (e.g., 5 minutes illumination time) luminescent chemical or combination of reactive chemicals. Suitable chemiluminescent compounds may have desired properties that include, without limitation, some or all of high light output (e.g., up to about 600 lumens); zero or very low toxicity to humans, and/or medical grade certification; and reactivity, such that the chemicals) is/are not luminescent until light is needed. Regarding the last property, in some embodiments the bougie 500 may contain two or more reactive chemicals that produce luminescence when mixed. The bougie 500 may thus require activation to be illuminated, as described further below. In other embodiments, the bougie 500 may be constantly lit.

In place of, or in addition to, the powered light source (and power supply) described with respect to the above example embodiments, the bougie 500 may include a transparent or translucent tube 520 disposed between the proximal end 502 and the distal end 504 of the bougie 500 and defining a luminescent chamber 510. In one embodiment, the tube 520 may extend from-end-to-end of the bougie 500. In another embodiment, the bougie 500 may include a proximal portion 512 comprising a solid polymer that is not reactive with the luminescent chemical(s). The proximal portion 512 may extend for a desired length and then connect or integrate with the tube 520. In one embodiment, the tube 520 may comprise the rest of the bougie 500, to the distal end 504. In another embodiment, the bougie 500 may further include a distal portion 514 that is a solid polymer like the proximal portion 512, and that extends for a desired length and connects or integrates with the tube 520.

In one embodiment, the tube 520 and the proximal portion 512 and distal portion 514, if present, may all have the same outer diameter, which is selected (as described above) from among common bougie sizes (e.g., 5 mm). The tube 520 further has an inner diameter and a thickness. The thickness of the tube 520 may be any suitable thickness that facilitates manufacture of the bougie 500, provides a chamber 510 of sufficient size to contain the luminescent chemical(s) (and, in various embodiments, other structures for implementing the chemiluminescence), and is desirably resistant to tearing, breaking, and leaking. In one embodiment, the bougie 500 may be extruded in a manner that allows the proximal portion 512, tube 520, and distal portion 514 to be created integrally in a continuous process. In another embodiment, the proximal portion 512 and/or the distal portion 514 may be attached to the corresponding end of the tube 520 by thermal bonding or via an adhesive. In one example, the portions 512, 514 are formed with projections 532, 534 having a diameter equal to the inner diameter of the tube 520; the projections 532, 534 may be coated with adhesive and inserted into the tube 520 to attach the portions 512, 514 to the tube 520, at least one of the portions 512, 514 being attached after the chamber 510 is filled with the luminescent chemical(s).

The material of the tube 520 is transparent or sufficiently translucent to transmit the desired amount of light from the chamber 510 out of the bougie 500. The tube 520 may further be composed to be resistant to damage from bending, particularly in embodiments where the bougie 500 must be bent to activate the chemiluminescence. For example, the chamber 510 may contain a mixture of CYALUME or diphenyl oxalate with a dye corresponding to the desired light color, and may further contain a breakable (e.g., glass) vial (not shown) containing hydrogen peroxide; when the bougie 500 is bent, the vial breaks and the previously separated contents of the chamber 510 mix and begin to luminesce. This is similar in operation to existing chemiluminescent signal devices, such as those sold under the trademark CHEMLIGHT as well as common glow sticks. The chemical(s) may further be selected so that they, separately and mixed, do not pose a hazard to humans who ingest them.

Another embodiment of the present lighted bougie (e.g., the illustrated example bougies 100, 200, 300 described above) may include one or more sensors embedded at or near the distal end of the bougie and providing a haptic feedback response, such as felt in video gaming controller technology, when the distal end passes over a tracheal ring, enhancing the "clicks" technicians now utilize in current bougie deployment. In still another embodiment, the bougie 100 may work in tandem with an ancillary auditory/illuminating "disc" or coin shaped sensing device that could be placed on the patient's neck and generate an indicator, such as a Lone or flashing light, when the bougie enters the field of detection of the sensing device. The sensing device need only be deployed when conditions such as body habitus, facial hair, presence of blood, lack of lighting, etc., make direct visualization of the trans-illumination impossible. A Doppler effect sensor may be used to further improve accuracy. Other sensors for determining appropriate placement of the lighted bougie of the Figures may be disposed at any suitable location on the bougie, such as at the distal end. In one embodiment, a carbon dioxide sensor may be used to detect the presence, at the distal end during insertion of carbon dioxide, which is not present in the esophagus and present in the trachea; thus, a signal from the sensor indicating the presence of carbon dioxide can be used to confirm the bougie is correctly inserted. In another embodiment, a pH detector may be used—if there is no change in pH during insertion of the bougie, the placement is in the trachea, while a change in pH indicates placement in the esophagus.

The embodiments presented herein for a lighted bougie greatly improve the ability of First Responders to quickly establish even a very difficult airway, thus improving patient outcomes. The disposable and compact nature would also make the device easy to maintain as a part of the normal complement of equipment on first responder rigs and in Emergency Departments. Selective trans-illumination at the distal end of the bougie illuminates the soft tissues adjacent to the trachea on the throat of the patient. Visualization of this illuminated area outside the body, coupled with the audible and tactile clicks heard or felt as the bougie passes by the tracheal rings assures proper placement of the bougie without the need for direct visualization of the vocal cords. The result is a much faster and verifiable intubation path. The structural design similarity to a standard bougie requires virtually no learning curve on the part of the user and the device can be used with or without the illuminating feature functioning. No additional steps are necessary to deploy or to ready the device for introduction of an endo-tracheal tube once the airway path is established. The design is such that once the path is established by means of the bougie, a traditional tracheal tube can be introduced over the bougie and will follow the path of the bougie leading to a proper intubation. The bougie can at that point be withdrawn through the tube and a resuscitation bag or Oxygen can be administered as with normal intubation.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Various features and advantages of the invention are set forth in the following claims.

What is claimed is:

1. A bougie for locating an airway of a patient, the bougie comprising:
a proximal end and a distal end, the bougie from the proximal end to the distal end having a standard diameter that enables a user of the bougie to pass the bougie through an endotracheal tube that is placed in the patient's airway using the bougie;
a fixed bend near the distal end; and
a light source having a sufficient light intensity and positioned to provide transillumination of an outer surface of the patient's neck when the bougie is positioned in the patient's airway, wherein the light source is configured to output light at an intensity of at least 600 lumens.

2. The bougie of claim 1, wherein the light source is a chemical light, the bougie further comprising a light-transmissive casing containing the chemical light and disposed relative to the distal end of the bougie such that light from the chemical light is visible on the outer surface of the patient's neck when the bougie is inserted into the patient's airway.

3. The bougie of claim 2, wherein the chemical light is configured to illuminate when the bougie is deployed and has a duration of about five minutes.

4. The bougie of claim 2, wherein the chemical light comprises one or more luminescent chemicals that, taken alone or together, are non-toxic to the patient, and the casing is a transparent or translucent tube defining a chamber that contains the one or more luminescent chemicals.

5. The bougie of claim 2, further comprising a proximal portion extending from the proximal end of the bougie to the casing.

6. The bougie of claim 5, wherein the proximal portion is a polymer that attaches to the casing.

7. The bougie of claim 5, wherein the proximal portion is integral with the casing.

8. The bougie of claim 5, further comprising a distal portion extending from the distal end of the bougie to the casing.

9. The bougie of claim 8, wherein the proximal portion, the casing, and the distal portion all have the same uniform diameter.

10. The bougie of claim 1, further comprising a device for detecting conditions at the distal end of the bougie, the device comprising one of a carbon dioxide sensor, a pH sensor, and an imaging device.

11. The bougie of claim 1, further comprising a haptic feedback device disposed near the distal end of the bougie, the haptic feedback device detecting when the distal end passes over a laryngeal ring and producing a haptic feedback response.

12. The bougie of claim 1, further comprising:
a housing disposed at the proximal end of the bougie and containing the light source;
a power source disposed at least partially within the housing, sized to pass through the endotracheal tube, and electrically connected and providing power to the light source; and
a fiber-optic cable extending from the housing to the distal end of the bougie and having a light-emitting portion approximate the distal end of the bougie, the fiber-optic cable and the light source oriented so that light emitted from the light source enters the fiber-optic cable, is transmitted to the light-emitting portion, and exits the fiber-optic cable to transilluminate the outer surface of the patient's neck.

13. The bougie of claim 12, wherein the fiber-optic cable is an end-emitting elastomeric solid rod that includes the fixed bend, the bougie further comprising a light-transmissive outer layer disposed over at least part of the fiber-optic cable and having the standard diameter.

14. The bougie of claim 13, wherein the housing is a cylindrical case having the standard diameter and abutting the outer layer.

15. The bougie of claim 13, wherein the outer layer is further disposed over the housing.

16. The bougie of claim 13, wherein the fiber-optic cable extends beyond the outer layer to form the distal end of the bougie, and is rounded and polished to emit light from the distal end of the bougie.

17. The bougie of claim 13, further comprising a coating disposed on the fiber-optic cable and restricting transverse transmission of light out of the fiber-optic cable.

18. The bougie of claim 17, further comprising one or more longitudinal interruptions formed through the coating, the one or more longitudinal interruptions allowing light to exit transversely from the fiber-optic cable.

19. A method for intubating a patient, the method comprising:

activating a lighted bougie comprising:

a proximal end and a distal end, the bougie from the proximal end to the distal end having a standard diameter that enables a user of the bougie to pass the bougie through an endotracheal tube that is placed in the patient's airway using the bougie;

a fixed bend near the distal end; and a light source having a sufficient light intensity and positioned to provide transillumination of an outer surface of the patient's neck when the bougie is positioned in the patient's airway;

positioning the distal end of the lighted bougie in the patient's mouth approximate the patient's trachea;

using the light emitted from the light source and visible through the patient's neck, inserting the lighted bougie into the patient's trachea to establish an airway path; and without removing any components of the lighted bougie:

positioning the endotracheal tube over the proximal end of the lighted bougie;

following the airway path of the lighted bougie, introducing the endotracheal tube over the lighted bougie and into the patient's trachea; and removing the lighted bougie from the patient's trachea and from the endotracheal tube.

20. The bougie of claim 1, wherein the bougie includes:

a fiber-optic cable wherein the fiber-optic cable and the light source are oriented so that light emitted from the light source enters the fiber-optic cable; and the fiber-optic cable includes a coating configured to block transmission of light out of a side of the fiber-optic cable, wherein the coating includes an interruption configured to allow light from the light source to pass through a wall of the bougie to provide the transillumination of the outer surface of the patient's neck when the bougie is positioned in the patient's airway.

\* \* \* \* \*